(12) United States Patent
Sanchez et al.

(10) Patent No.: US 6,548,645 B1
(45) Date of Patent: Apr. 15, 2003

(54) IMMUNOASSAY FOR 2-OXO-3-HYDROXY LSD

(75) Inventors: Anthony de Jesus Sanchez, Concord, CA (US); David Davoudzadeh, Pleasanton, CA (US); William A. Coty, Fremont, CA (US)

(73) Assignee: Microgenetics Corporation, Fremont, CA (US)

( * ) Notice: Subject to any disclaimer, the term of this patent is extended or adjusted under 35 U.S.C. 154(b) by 0 days.

(21) Appl. No.: 09/596,291

(22) Filed: Jun. 16, 2000

Related U.S. Application Data

(60) Provisional application No. 60/140,110, filed on Jun. 18, 1999.

(51) Int. Cl.[7] ............... C07K 16/44; C07K 17/06; C07D 251/28; C07D 457/06; G01N 33/533; G01N 33/534; G01N 33/535
(52) U.S. Cl. ................ 530/405; 435/6; 435/188; 436/525; 436/533; 436/544; 436/545; 436/546; 530/388.9; 530/389.8; 530/391.9; 530/404; 530/807; 544/212; 544/217; 544/218; 546/69
(58) Field of Search ................ 435/188, 6; 436/546, 436/545, 525, 533, 544; 530/403, 405, 388.9, 389.8, 391.9, 404, 807; 546/69; 544/212, 217, 218

(56) References Cited

U.S. PATENT DOCUMENTS 6,063,908 A * 5/2000 Salamone et al.
6,207,396 B1 * 3/2001 Sigler et al.

FOREIGN PATENT DOCUMENTS

| EP | 880029 | * | 2/1998 |
| WO | WO9719100 | | 5/1997 |
| WO | 98/26644 | * | 6/1998 |

OTHER PUBLICATIONS

Yuji Nakahara et al., *Detection of LSD and Metabolite in Rat Hair and Human Hair*, Journal of Analytical Toxicology, vol. 20, Sep. 1996, pp. 323–329.
Reuschel, Scott A. et al., *Quantitative Determination of LSD and a Major Metabolite, 2–Oxo–3–Hydroxy–LSD, in Human Urine by Solid–Phase Extraction and Gas Chromatography–Tandem Mass Spectrometry*, Journal of Analytical Toxicology, vol. 23, Sep. 1999, pp. 306–312.
Reuschel, Scott A. et al., *Recent advances in chromatographic and mass spectrometric methods for determination of LSD and its metabolites in physiological specimens*, Journal of Chromatography B, 733 (1999), pp. 145–159.
Zhuyin Li et al., *New Synthesis and Characterization of (+) – Lysergic Acid Diethylamide (LSD) Derivatives and the Development of a Microparticle–Based Immunoassay for the Detection of LSD and Its Metabolites*, Bioconjugate Chem., 1997, 8, pp. 896–905.
Chad C. Nelson et al., *Chromatographic and mass spectrometric methods for determination of lysergic acid diethylamide (LSD) and metabolites in body fluids*, Journal of Chromatography, 580, 1992, pp. 97–99.
Troxler, F. et al., *Oxydation von Lyergsaure–Derivaten in 2,3–Stellung*, Helvetica Chimica Acta, vol. 42, (1959), pp. 793–802.

* cited by examiner

Primary Examiner—Mary E. Ceperley
(74) Attorney, Agent, or Firm—Wood, Herron & Evans, L.L.P.

(57) ABSTRACT

To improve the detection of LSD, and LSD metabolites in biological samples, antibodies are raised to 2-oxo-3-hydroxy-LSD conjugated to a protein carrier. Selected antibodies are matched with an immunoassay reagent in which the 2-oxo-3-hydroxy-LSD is conjugated in the same position to a labeling or separation means. The set of reagents can be used in immunoassays for detecting or confirming the presence of LSD or LSD metabolites in a sample potentially containing interfering substances.

9 Claims, 2 Drawing Sheets

IMMUNOASSAY FOR 2-OXO-3-HYDROXY LSD

CROSS-REFERENCE TO RELATED APPLICATION

This application claims the benefit of the filing date of Provisional U.S. Patent Application No. 60/140,110 entitled "Immunoassay for 2-oxo-3-hydroxy LSD" and filed on Jun. 18, 1999.

TECHNICAL FIELD

This invention relates generally to the field of the detection of drugs and drug metabolites in biological samples. Specifically, the invention relates to the generation of antibodies that specifically bind to a metabolite of LSD, 2-oxo-3-hydroxy-LSD, or those that recognize both the metabolite and the parent drug LSD. The compositions and methods of the present invention are particularly useful for confirming the presence of LSD or LSD metabolites in a sample potentially containing interfering substances.

BACKGROUND OF THE INVENTION

Although there is widespread public perception that use of LSD is no longer a societal problem, there is considerable evidence that this illicit drug continues to be used, and in some segments of the population, its use is increasing (Bonner, *Drug Detection Report*. 1:5 (1992)). LSD was one of the 20 controlled substances most commonly encountered in emergency rooms across the nation in 1985, reflecting continuing abuse and trafficking of this illicit drug. In the United States, seizures of LSD by the Drug Enforcement Agency doubled in 1990 over the previous year, and in England, seizures of LSD have steadily increased since mid-1988 (*Microgram* 23:228 (1990)). Further causes for concern are reports that LSD is particularly popular among adolescents, and in some areas, it exceeds cocaine in popularity (Seligmann, *Newsweek*, February 3rd, p. 66, (1992)). Factors that have contributed to the continued use of LSD are its wide availability, low cost, and the difficulty of detecting LSD use by analysis of body fluids.

Despite the long history of abuse associated with LSD, little is known concerning the disposition of LSD in humans. The lack of pharmacokinetic data on LSD is partly due to the technical difficulty of detecting and measuring the drug in physiological specimens. LSD is not considered highly toxic, although at least two cases where death was apparently a result of LSD toxicity have been reported. However, the major reason many consider LSD to be highly dangerous is that it can have serious psychological and psychotic effects which sometimes cause users to commit irrational acts resulting in injury or death. LSD is an extremely potent psychedelic drug that acts primarily on the central nervous system; only the d-isomer of the drug is pharmacologically active. Oral doses as low as 25 $\mu$g can cause central nervous system disturbances such as hallucinations, distortions in sensory perception, mood changes and dream-like thought processes, as well as psychotic reactions in apparently predisposed individuals. Therefore, concentrations of LSD and LSD metabolites in blood and urine are likely to be very low. The detection of LSD in body fluids of users is especially difficult because the quantities typically ingested are very small and because the drug is rapidly and extensively converted to metabolic products. Furthermore, the drug's low volatility, its thermal instability, and its tendency to undergo adsorptive losses during gas chromatographic analysis all contribute to the difficulty of developing a method for confirmation of LSD in body fluids.

LSD is a natural product of the rye fungus Claviceps and was first prepared synthetically in 1938. Its psychological effects were discovered following accidental ingestion. Chemically, LSD is an ergot alkaloid and, like other compounds of this class, contains lysergic acid as the basis of its structure. Structurally similar to serotonin (5-hydroxytryptamine), LSD is thought to exert its psychotomimetic effects through antagonism of serotonin activity in the brain stem. Little is known about the tissue distribution, metabolism and excretion of LSD in humans. LSD is absorbed fairly rapidly by the gastrointestinal tract, and its plasma half-life has been calculated to be about 3 hours in man. Animal studies indicate that LSD is inactivated via hepatic oxidation. It is extensively metabolized with only negligible amounts of unchanged drug appearing in the urine and feces, with most of the metabolites being excreted in the urine. Possible metabolic transformations may be hydrolysis to lysergic acid, N-demethylation to nor-LSD and oxidation to 2-oxo-LSD. Studies with urine samples from human volunteers receiving LSD demonstrate that the drug or its closely related metabolites can be detected in the urine by radioimmunoassay (RIA) for several days following administration.

Although continued illicit use of LSD has stimulated efforts to develop effective analytical methods for the detection of the drug and its metabolites in body fluids from suspected LSD users, the methods currently available are complicated, time-consuming, expensive to perform and plagued by other problems. These methods include high performance liquid chromatography (HPLC), gas chromatography/mass spectrometry (GC/MS) and radioimmunoassay. One problem faced by laboratories involved in the determination of LSD is the strong tendency for LSD and derivatized LSD to undergo adsorptive losses when subjected to gas chromatography. This behavior often prevents detection of the drug at the sub-nanogram/milliliter concentrations normally encountered in body fluids from LSD users.

Commercial RIAs for LSD are available from several sources, including ABUSCREEN LSD assay (® Roche Diagnostics Systems, Nutley, N.J.) and COAT-A-COUNT LSD assay (® Diagnostic Products Corp., Los Angeles, Calif.), and these products serve as a useful and relatively inexpensive method of screening for the presence of the drug. However, RIAs are not totally specific for LSD, so that an RIA-positive specimen still has to be confirmed by a second and more specific assay if the results of the analysis could have punitive consequences. The manufacturers' recommended cut-off concentration for considering a sample positive for LSD is 0.5 ng/ml, although lower cut-offs have been used in investigations where legal consequences were not a concern. The actual concentration of LSD in RIA-positive urine specimens is generally lower than that indicated by the RIA, and often considerably lower. Presumably the higher concentrations indicated by RIA are due to the cross-reactivity of LSD metabolites to the RIA antisera, but this conclusion cannot be substantiated until the major LSD metabolites in urine have been identified and their cross-reactivities determined.

In testing for other drugs of abuse, immunoassays, particularly competitive binding immunoassays, have proven to be especially advantageous. In competitive binding immunoassays, an analyte in a biological sample competes with a labeled reagent, or analyte analog, or tracer, for a limited number of receptor binding sites on antibodies specific for the analyte and analyte analog. Enzymes such as $\beta$-galactosidase and peroxidase, fluorescent molecules such as fluorescent compounds, and radioactive compounds such as $^{125}I$ are common labeling substances used as tracers. The concentration of analyte in the sample determines the amount of analyte analog which will bind to the antibody. The amount of analyte analog that will bind is inversely proportional to the concentration of analyte in the sample, because the analyte and the analyte analog each bind to the antibody in proportion to their respective concentrations. The amount of free or bound analyte analog can then be determined by methods appropriate to the particular label being used.

One type of competitive binding immunoassay is based upon the reassociation of enzymatically inactive polypeptide fragments to form active enzyme as a step of generating a detectable signal utilized to determine the amount of analyte present in a sample. This type of assay, known as cloned enzyme donor immunoassay (CEDIA), is described in U.S. Pat. No. 4,708,929. In particular, a β-galactosidase enzyme donor polypeptide combines with a β-galactosidase enzyme acceptor polypeptide to form active β-galactosidase enzyme. Conjugating a hapten, or a small analyte or an analyte analog, to the enzyme donor polypeptide at certain sites does not affect the ability to form active β-galactosidase by a complementation reaction and hence does not affect the rate of β-galactosidase activity when in the presence of a substrate for β-galactosidase. However, when the enzyme donor-hapten conjugate is bound by anti-analyte antibody, the complementation rate is impeded, and thereby the enzyme-catalyzed reaction rate during the initial phase of the reaction is reduced. This reduction in enzyme-catalyzed reaction rate can be monitored and has been used successfully to determine a plurality of analytes using the principle of competitive inhibition whereby enzyme donor-analyte conjugate present in a reaction mixture and analyte present in a sample compete for anti-analyte antibody prior to the addition of enzyme acceptor. The complementation rate of β-galactosidase formation, and hence enzyme-catalyzed reaction rate, is increased as the amount of analyte present in the sample is increased.

The preparation of antibodies to LSD for use in immunoassays to determine the drug has been accomplished by several different approaches. One approach has been to couple the carboxyl group of lysergic acid directly to an immunogenic carrier protein, i.e. poly(L-lysine) or human serum albumin using carbodiimides. See Van Vunakis, *Proc. Nat. Acad. Sci.*, 68:1483–87 (1971); Loeffler, *J. Pharm. Sci.* 62:1817–20 (1973); and Voss, *Psychopharmacologia* 26:140–45 (1972). This approach was used in developing early RIA methods for LSD determination, but the antibodies that were produced were characterized by poor specificity for LSD and high cross-reactivities with other ergot alkaloids.

A second approach has been to couple LSD to an immunogenic carrier protein via one of the ethyl side chains at the 8-position (Ratcliffe, *Clin. Chem.* 23:169–74 (1977)). In another approach, bis-diazo benzidine was used to couple the carrier proteins via an aromatic substitution (Luderer, *Bull. New Jersey Acad. Sci.* 19:8–10 (1974)).

Finally, LSD has been coupled to an immunogenic carrier protein using a reaction between LSD, formaldehyde and bovine serum albumin. See Castro, *Res. Commun. Chem. Pathol. Pharmacol.* 6:879–86 (1973); Taunton-Rigby, *Science* 181:165–6 (1973); and Ratcliffe, *Clin. Chem.* 23:169–74 (1977); see also Orchin, *The Vocabulary of Organic Chemistry*, John Wiley & Sons, NY, p. 385 and p. 501, Figure 13.790; Furniss, *Vogel's Textbook of Practical Organic Chemistry*, 4th Ed., Longman Scientific & Technical and John Wiley & Sons, NY, p. 813 (1978); and Mundy, *Name Reactions and Reagents in Organic Synthesis*, John Wiley & Sons, NY, p.137 (1988). The reaction product is not well-defined.

More recently, Salamone, S. J. et al. in *Bioconjugate Chem* 8: 896–905 (1997) reported the synthesis of an array of LSD immunogens by conjugating LSD analogs derivatized through the indole nitrogen (N-1) or N-6 position to a carrier. The antibodies generated by these immunogens exhibit broad reactivity toward LSD and several LSD metabolites. Whereas the antibodies react strongly to LSD, the antibodies have low cross-reactivity (in the range of only 30–45%, molar ratio) to several LSD metabolites, including 2PATENT -oxo-3-hydroxy-LSD. While Salamone, S. J. et al. failed to recognize that 2-oxo-3-hydroxy-LSD is indeed an endogenous LSD metabolite as oppose to be a "tentative" metabolite, it is now becoming evident that 2-oxo-3-hydroxy-LSD may be the most prevalent metabolite of LSD. Thus, there remains a considerable need for compositions and methods applicable for generating antibodies specific for the LSD metabolite, 2-oxo-3-hydroxy-LSD. The production of these antibodies would greatly facilitate detecting the presence of LSD or LSD metabolites in a clinical sample, and confirming LSD abuse in a clinical setting.

DISCLOSURE OF THE INVENTION

The present invention provides compositions and methods applicable for generating antibodies specific for a LSD metabolite, 2-oxo-3-hydroxy-LSD, or its derivatives. This invention also provides the uses of these antibodies for the detection or measurement of LSD or 2-oxo-3-hydroxy-LSD in samples obtained from subjects who may have been exposed to LSD. In various embodiments, the system allows for detection of both the parent substance and natural metabolites as they may be formed within the subject or secreted into a biological fluid, particularly urine. The sensitivity and specificity of the reagents may be used in diagnostic-grade immunoassays for screening of drugs of abuse in a clinical setting.

In one embodiment, the present invention provides novel hapten derivatives of the formulas

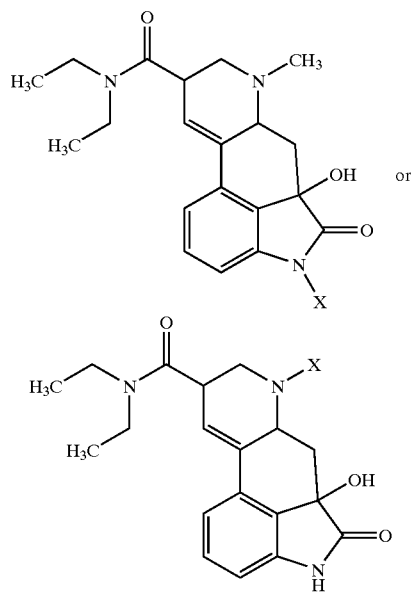

wherein X is —L$^1$—Z, where L$^1$ is a linker containing at least one carbon atom; wherein Z is selected from the group consisting of the moieties

—NH$_2$,
—COOH,
—SH,

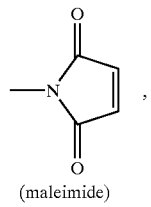
(maleimide)

—NH—C(=O)—L$^2$—M,

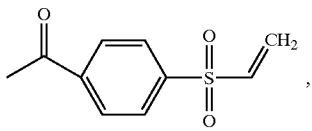,

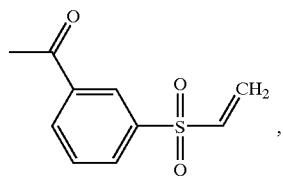,

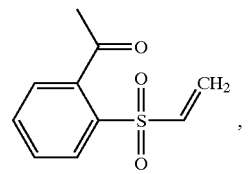,

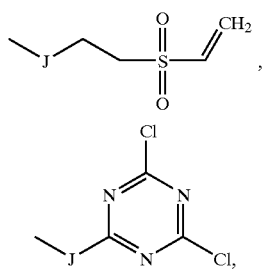, a moiety which reacts with a protein to form a covalent bond, or any combination or repetition of the aformentioned moieties; where L$^2$ is a linker containing at least one carbon atom; where M is halide or maleimide; and wherein J is —O—, —S—, —NH— or —CH$_2$—. L$^1$ and L$^2$ are preferably independently selected from the group consisting of C$_1$–C$_{20}$ hydrocarbon chains, containing zero to ten heteroatoms selected from the group consisting of N, O, and S.

In another embodiment, the present invention provides novel hapten derivatives of the formulas

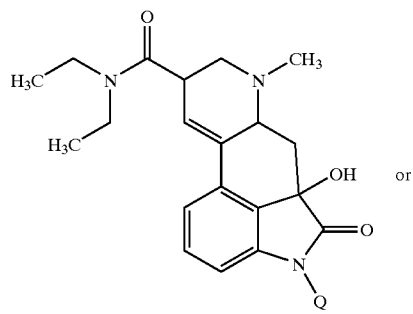 or

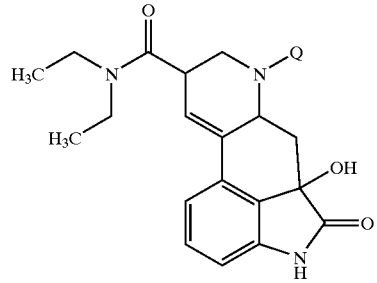

where Q is —L$^1$—G, L$^1$ is a linker containing at least one carbon atom, and G is selected from the group consisting of fluorescent, chemiluminescent, phosphorescent, and chromophoric compounds, a fluorescence quenching group, a radioisotopically labeled group, an electrochemically active group, an electrochemiluminescent group, a group that undergoes a change in fluorescence, phosphorescence, chemiluminescence or electrochemical property upon binding, peptides, proteins, protein fragments, immunogenic carriers, enzymes, enzyme donors, enzyme inhibitors, enzyme substrates, enzyme cofactors, enzyme prosthetic groups, solid particles, gold particles, antibodies, and nucleic acids. L$^1$ is preferably selected from the group consisting of C$_1$–C$_{20}$ hydrocarbon chains, containing zero to ten heteroatoms selected from the group consisting of N, O, and S.

In another embodiment, the present invention provides a method of generating an antibody specific for a novel LSD metabolite, 2-oxo-3-hydroxy-LSD, or its derivatives. The method involves preparing 2-oxo-3-hydroxy-LSD immunogens having the formulas shown above, and immunizing an appropriate host to elicit an immunogen-specific immune response.

In yet another embodiment, the invention provides an antibody that binds specifically to 2-oxo-3-hydroxy-LSD or a derivative thereof. The antibody can be specific for the LSD metabolite, 2-oxo-3-hydroxy-LSD (as distinct from the parent drug LSD), or it can be specific for both the parent drug LSD and the metabolite. The antibody can be polyclonal or monoclonal, non-conjugated or conjugated to a detectable label.

In a separate embodiment, the invention provides systems that permit detection of 2-oxo-3-hydroxy-LSD, either alone or in combination with LSD itself. Testing for 2-oxo-3-hydroxy-LSD permits the practitioner to detect possible use of LSD by the subject over a longer period of time than by testing for LSD alone. Specifically, the invention includes a reagent system for use in an immunoassay, comprising an antibody of this invention along with a labeled competitive binding compound (typically an LSD derivative, or a derivative of 2-oxo-3-hydroxy-LSD) that competes with the substance being tested for binding to the antibody. The reagent system can also optionally include additional components useful in conducting an assay, such as reagents for developing a detectable signal from the labeled compound following the competition reaction, buffers, standards, or written instructions. Different reagents can be premixed in any workable combination.

Also embodied in the present invention is an immunoassay method for determining the possible presence of 2-oxo-3-hydroxy-LSD in a sample. Such method involves preparing a reaction mixture comprising the sample, an antibody of this invention, and a labeled competitive binding compound capable of competing with 2-oxo-3-hydroxy-LSD. The amount of label bound to the antibody in the reaction mixture is then determined by a suitable detection technique, such as separating the complexes and measuring the label, or measuring an effect on the labeled compound as a result of being bound to antibody, such as a change in fluorescence or enzyme activity. The amount can be correlated with exposure of the subject to LSD, and if appropriate, further steps can be taken to distinguish between LSD and the metabolite, 2-oxo-3-hydroxy-LSD. This method can be employed to confirm previous exposure to LSD over a longer period of time than is possible by testing for LSD alone. Featured reagents for conducting such immunoassay include the following: competitive binding compounds in which the label is conjugated to the LSD derivative or derivatives of 2-oxo-3-hydroxy-LSD; antibodies that are specific for 2-oxo-3-hydroxy-LSD or specific for both LSD and the metabolite; CEDIA® assay system; and LSD or 2-oxo-3-hydroxy-LSD conjugated to enzyme donors of β-galactosidase.

Further provided by the present invention are assay methods for confirming the presence of the analyte, 2-oxo-3-hydroxy-LSD, and distinguishing it from interfering substances potentially present in a test sample. Samples giving a positive reaction in a direct immunoassay test are treated with a neutralizing antibody that inhibits reactivity of the true analyte, but not the interfering substance. Thus, samples giving a positive reaction in the direct test but decreased reaction in the confirmation test are marked as containing the true analyte. Samples giving a positive reaction of roughly equivalent magnitude in both the direct and confirmation test are marked as containing an interfering substance. In one embodiment, a direct assay is conducted to determine the amount of analyte and/or interfering substance in the sample. The same sample or a duplicate is treated with a neutralizing antibody in an amount sufficient to remove the analyte but not the potential interfering substance, and an assay is conducted on the treated sample. The amount detected is then compared between the treated and untreated sample. In another embodiment, the assay proceeds by preparing a reaction mixture that comprises the test sample, a detecting antibody, and a competitive binding compound, wherein the detecting antibody binds a hapten derivative in a manner that is specifically inhibitable by the analyte, 2-oxo-3-hydroxy-LSD. The amount of the detecting antibody bound to the competitive binding compound is measured. To conduct the confirmation part of the test, the same sample is treated with a neutralizing antibody, or else a duplicate sample is treated with a neutralizing antibody before, during or after the direct test. The neutralizing antibody prevents the analyte but not all the interfering substance in the sample from being available to bind the detecting antibody when an assay is conducted on the treated sample. The results from the direct and the confirmatory test are then compared. The presence of the true analyte, 2-oxo-3-hydroxy-LSD, is confirmed if there is a significant effect on the result due to use of the neutralizing antibody. Featured types of confirmatory assays of this invention include bidirectional antibody type confirmatory assays and adsorption type confirmatory assays.

Kits employed for conducting the confirmatory assays comprise a detecting antibody for the analyte, 2-oxo-3-hydroxy-LSD, and a neutralizing antibody for the analyte. The neutralizing antibody preferentially binds the analyte in comparison with the interfering substance. The neutralizing antibody is preferably either aliquoted in an amount sufficient to remove the analyte but not all the interfering substance from the sample, or a written indication is provided as to the amount required. The set of reagents also typically comprises a competitive binding compound, with the property that the detecting antibody binds the hapten derivative in a manner that is specifically inhibitable by the analyte and the interfering substance. An exemplary competitive binding compound is a hapten derivative, such as a hapten-protein conjugate or a hapten labeled with a radioisotope or fluorochrome.

Further aspects of the invention and desirable characteristics of the reagents and assay methods will be apparent from the description that follows and the appended claims.

BRIEF DESCRIPTION OF THE DRAWINGS

The present invention will be better understood by reference to the following detailed description of the invention when considered in combination with the drawings that form part of the specification, wherein.

DETAILED DESCRIPTION

Figure 1:
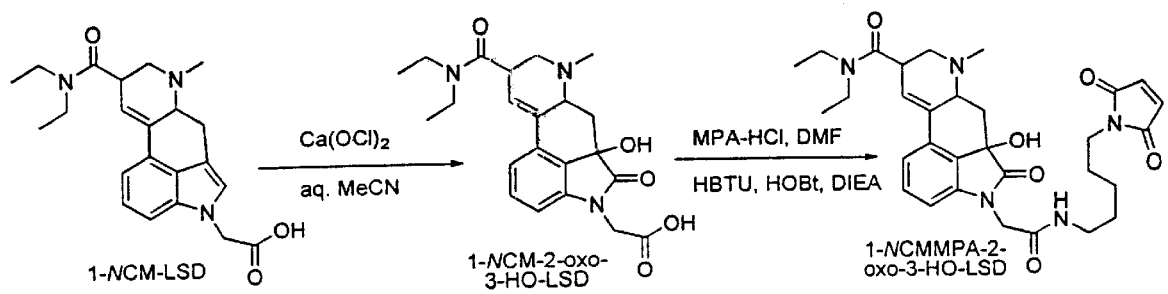
FIG. 1 illustrates a particular synthetic scheme for preparing l-NCMMPA-2-oxo-3-hydroxy-LSD.

A central aspect of the present invention is the generation of antibodies that are specific for the novel LSD metabolite, 2-oxo-3-hydroxy-LSD, or that are specific for both LSD and the metabolite. The metabolite 2-oxo-3-hydroxy-LSD is detectable in biological fluids over a longer period of time than the parent drug LSD. Thus, the methods and reagents provided in the disclosure considerably extend the window in which a previous LSD exposure can be detected.

Particular technical terms used in this disclosure are defined as follows:

The term "hapten" as used in this disclosure denotes a homogeneous or heterogeneous chemical compound, generally <5,000 mol wt and typically <1,000 mol wt, with the property that a complex between the hapten and one hapten-specific antibody will inhibit the binding of a second hapten-specific antibody, regardless of whether the second antibody is different from the first or recognizes the hapten from a different orientation. In other words, a hapten has a functional valence of one with respect to antibody binding. A "hapten" by itself is typically ineffective in stimulating antibody formation, but can be bound by antibodies. LSD and its metabolite 2-oxo-3-hydroxy-LSD are exemplary haptens.

A "hapten derivative" denotes a compound that contains a feature of a hapten that is specifically recognizable by an anti-hapten antibody, and has been derivatized to provide it with an additional property of interest. Examples of hapten derivatives include a hapten containing a chemically-reactive group, a hapten covalently linked to a protein, and a hapten covalently linked to a solid surface (where the linkage is a covalent bond or a linking group of one or more atoms, such as may be formed by chemical synthesis or conjugation using a cross-linking agent). Other examples of hapten derivatives are haptens that have been chemically derivatized with a labeling feature, such as fluorescent, chemiluminescent, phosphorescent, and chromophoric compounds, a fluorescence quenching group, a radioisotopically labeled group, an electrochemically active group, an electrochemiluminescent group, a group that undergoes a change in fluorescence, phosphorescence, chemiluminescence or electrochemical property upon binding, peptides, proteins, protein fragments, immunogenic carriers, enzymes, enzyme donors, enzyme inhibitors, enzyme substrates, enzyme cofactors, enzyme prosthetic groups, solid particles, gold particles, antibodies, and nucleic acids. A hapten derivative need not be functionally monovalent with respect to antibody binding. For example, a hapten-protein conjugate can optionally contain a plurality of haptens, depending on its intended role, and the valence will approach that of the conjugation ratio.

"2-oxo-3-hydroxy-LSD" is a modified form of LSD, formed by oxidation of the parent compound at C2 and C3 positions of the indole ring during in vivo metabolism of LSD. The chemical structure of 2-oxo-3-hydroxy-LSD is represented by the formula:

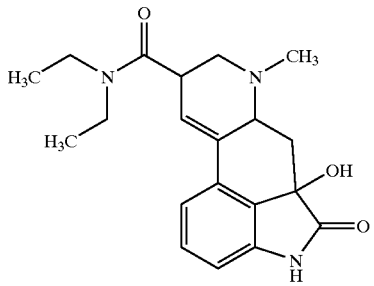

The 2-oxo-3-hydroxy-LSD metabolite may appear in blood (tested as serum or plasma) or other internal bodily fluid, or excreted into any external bodily fluid, such as urine, bile or saliva. A biological sample includes but is not limited to the internal bodily fluids and the external bodily fluids.

A "carrier", as the term is used herein, is an immunogenic substance, commonly a protein, that can join with a hapten, thereby enabling the hapten to stimulate an immune response. Carrier substances include proteins, glycoproteins, complex polysaccharides and nucleic acids that are recognized as foreign and thereby elicit an immunologic response from the host. An exemplary carrier is keyhole limpet hemocyanin (KLH).

The term "immunogenic" as used herein refers to substances capable of producing or generating an immune response in a host organism.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

A "complex" is an association of chemical compounds or moieties together by non-covalent bonds, possibly in a reversible fashion. Examples are an enzyme-substrate complex (an association of an enzyme and one or more substrates that is the reacting moiety in an enzyme-catalyzed reaction), an antigen-antibody complex, a hapten-antibody complex, or an active enzyme complex of β-galactosidase formed by complementation of an enzyme donor and an enzyme acceptor. A "stable complex" is a complex that persists at least as long as it takes the presence of the complex to be measured by the intended method.

An "enzyme acceptor" (EA) is an enzymatically inactive, polypeptide fragment of an enzyme. Exemplary is an EA of β-galactosidase produced by a deletion mutant of the β-galactosidase gene. When the EA is combined or associated with an enzyme donor, it is capable of forming active enzyme by the process of complementation.

An "enzyme donor" (ED) is an enzymatically inactive polypeptide fragment of an enzyme. Exemplary is an ED of β-galactosidase. The ED comprises a peptide sequence capable of combining or associating with an EA to form an active enzyme.

The term "derivative" refers to a chemical compound or molecule obtainable from a parent compound or molecule such as LSD and 2-oxo-3-hydroxy-LSD metabolite by one or more chemical reactions. A 2-oxo-3-hydroxy-LSD derivative comprises the same or equivalent epitopes recognizable by an antibody specific for the parent compound, 2-oxo-3-hydroxy-LSD, as determined by an immunoassay. Such derivative can be a 2-oxo-3-hydroxy-LSD conjugate or an adduct. When one substance is described as "conjugated" to another, then they are attached together in a stable arrangement, preferably through a covalent linkage, and optionally through a bridging structure.

The term "antibody" as used in this disclosure refers to both polyclonal and monoclonal antibodies. The ambit of the term explicitly encompasses not only intact immunoglobulin molecules, but also such fragments and derivatives of immunoglobulin molecules as may be prepared by techniques known in the art, and retaining the antibody activity of an intact immunoglobulin. Examples of antibodies other than intact immunoglobulins are provided below. In this context, "antibody activity" refers to the ability of an antibody to bind a specific antigen in preference to other potential antigens via the antigen combining site located within a variable region of an immunoglobulin.

An antibody binds "specifically" to a particular substance such as 2-oxo-3-hydroxy-LSD if it binds with greater affinity or avidity than it binds to other unrelated substances in a typical test sample. One embodiment of the invention encompasses antibodies specific to 2-oxo-3-hydroxy-LSD or its derivatives. Typically, an antibody that is specific for 2-oxo-3-hydroxy-LSD or its derivatives exhibits less than about 50% cross-reactivity with metabolites other than 2-oxo-3-hydroxy-LSD as determined by a quantitative immunoassay. Preferably, the specific antibody is also less than about 30% cross-reactive, more preferably less than about 20%, even more preferably less than about 10%, and yet more preferably less than about 1% cross-reactive with an LSD metabolite other than 2-oxo-3-hydroxy-LSD. Examples of these non-2-oxo-3-hydroxy-LSD metabolites include N-desmethyl-LSD, 13-hydroxy-LSD, 14-hydroxy-LSD, LSD-13-OH-glucuronide and LSD-14-OH-glucuronide. Where the assay is desired for direct quantitation of 2-oxo-3-hydroxy-LSD, cross reactivity on a molar basis of the anti-2-oxo-3-hydroxy-LSD antibody to the parent drug LSD should be less than about 10%, preferably less than about 5%, more preferably less than about 1%, still more preferably less than about 0.1%.

In alternative embodiments of the invention, certain antibodies of this invention can bind to 2-oxo-3-hydroxy-LSD and can also bind to the parent drug LSD or its derivatives, or other metabolites of LSD and their derivatives. These antibodies are preferable for use when maximum sensitivity of the assay to detection of LSD abuse is the objective, and higher cross-reactivity of the anti-2-oxo-3-hydroxy-LSD antibody to LSD is desirable. This cross-reactivity can be between about 50% to about 150%, more preferably about 50% to about 100% or about 50% to about 75% or about 75% to about 100%, or alternatively more preferably about 100% to about 150% or about 100% to about 125% or about 125% to about 150%, or alternatively about 60% to about 140% or about 70% to about 130% or about 80% to about 120% or about 90% to about 110%. Preferred minimum values of cross-reactivity to LSD are about 50%, about 60%, about 70%, about 80%, and about 90%. Preferred maximum values of cross-reactivity to LSD are about 150%, about 140%, about 130%, about 120%, and about 110%. Most preferably, the cross-reactivity is 100% in this embodiment.

A "detecting antibody" is an antibody that is used in an immunoassay for detecting the presence of an analyte in a sample. The detecting antibody will be able to distinguish between the analyte and other substances that may be present in the sample, although there may be a subset of substances that cross-react. The immunoassay is performed by contacting the antibody with the sample under conditions that permit the antibody to form a complex with any analyte present, and measuring any complex formed.

A "neutralizing antibody" is an antibody that is used in an assay for confirming the presence of an analyte in a sample. The neutralizing antibody will be able to bind the analyte and thereby prevent it from giving a positive reaction in an assay, particularly an immunoassay conducted with a detecting antibody.

"Cross reactivity" is determined in a quantitative immunoassay by establishing a standard curve using known dilutions of the target analyte. The standard curve is then used to calculate the apparent concentration of the interfering substance present in various known amounts in samples assayed under similar condition. The cross reactivity is the apparent concentration of analyte divided by the actual concentration of cross-reactant multiplied by 100. The preferred immunoassay for determining cross-reactivity is a CEDIA® type enzyme complementation assay.

An "analyte" is a substance of interest to be measured in a sample using a particular assay system. It may have any size, structure, or valence irrespective of components used in the assay system, unless otherwise specified or required. A "small molecule analyte" has a size of <5,000 mol wt and typically <1,000 mol wt.

A "competitive binding compound" in the context of an immunoassay for an analyte in a sample refers to a compound which binds the detecting antibody of the immunoassay in a manner that is inhibitable by the analyte.

The term "enzyme immunoassay" includes any immunoassay in which an enzyme is part of the detection system. The enzyme may be simply a tag for an active component in the reaction mixture, or it may be assembled, disassembled, activated, or deactivated in the course of the reaction. The presence of the analyte of interest in the sample may be directly or inversely correlated with enzyme activity.

"Luminescence" is the term commonly used to refer to the emission of light from a substance for any reason other than a rise in its temperature. In general, atoms or molecules emit photons of electromagnetic energy (e.g., light) when then move from an "excited state" to a lower energy state (usually the ground state); this process is often referred to as "radiative decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a singlet-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions, although some fluorophores have long enough lifetimes to permit measurement of time-resolved fluorescence. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" of the present invention may have any one of the above-described properties.

A "substance of abuse" is a chemical not naturally occurring in the body and administered to the body in contravention of the provisions of a criminal or disciplinary code, terms of employment, terms of participation in a particular activity such as an athletic competition, or which seriously impairs an activity (such as the operation of a vehicle) to the peril of the public or those in the vicinity of the abuser, or which provides the abuser with an unfair physical or intellectual advantage in a competitive arena. LSD is an illustrative substance of abuse.

The phrase "a linker containing at least one carbon atom" is meant to refer to any generic linking group between two other groups, e.g., a linker between hapten and protein, or a linker between hapten and a functional group suitable for attachment to another molecule, which contains at least one carbon atom. The linker group is preferably a $C_1$–$C_{20}$ hydrocarbon chain containing zero to ten heteroatoms selected from the group consisting of N, O, and S, and which contains at least as many carbon atoms as heteroatoms. Examples of such generic linking groups include, but are not limited to, —O—$(CH_2CH_2O)_n$—, where n is an integer between 1 and 10 (i.e., a polyethylene glycol linker); —$CH_2CH_2$-phenyl-$CH_2CH_2$— (in ortho, meta, or para connection); —$CH_2CH_2$—CONH—$CH_2CH_2$— (i.e., an amide linkage), —C(=O)—CHS—NH— (i.e., an amino acid linker, where S is a naturally or non-naturally occurring amino acid side chain) or indeed, any straight-chain, branched, cyclic, or combination of straight-chain, branched, or cyclic linking group that will serve as a covalent linkage between the two other groups. Preferred linkers are $C_1$–$C_{20}$ alkyl groups.

Particular chemical structures represented in this disclosure include all stereoisomers, tautomers, salts, and protonated and deprotonated forms unless otherwise indicated.

Antibodies and Immunoassay Reagent Systems of the Invention

The antibodies embodied in this invention encompass polyclonal antibodies and monoclonal antibodies that bind specifically to 2-oxo-3-hydroxy-LSD or its derivatives. The antibodies include but are not limited to mouse, rat, rabbit or human antibodies. The monoclonal antibodies of this invention refers to antibody compositions having a homogenous antibody population. It is not intended to be limited as regards to the source of the antibody or the manner in which it is made. This invention also encompasses functionally equivalent antibodies and fragments thereof. A functional equivalent antibody or a fragment of the invention antibody retains the desired binding specificity to 2-oxo-3-hydroxy-LSD or its derivatives.

Antibody fragments include the Fab, Fab', F(ab')$_2$, and Fv regions, or derivatives or combinations thereof. Fab, Fab', and F(ab')$_2$ regions of an immunoglobulin may be generated by enzymatic digestion of the monoclonal antibodies using techniques well known to those skilled in the art. Fab fragments may be generated by digesting the monoclonal antibody with papain and contacting the digest with a reducing agent to reductively cleave disulfide bonds. Fab' fragments may be obtained by digesting the antibody with pepsin and reductive cleavage of the fragment so produced with a reducing agent. In the absence of reductive cleavage, enzymatic digestion of the monoclonal with pepsin produces F(ab')$_2$ fragments.

It will further be appreciated that encompassed within the definition of antibody fragment is single chain antibody that can be generated as described in U.S. Pat. No. 4,704,692, as well as chimeric antibodies. Chimeric antibodies are those in which the various domains of the antibodies' heavy and light chains are coded for by DNA from more than one species.

The immunogen employed for generating the antibodies of the present invention comprises 2-oxo-3-hydroxy-LSD or a derivative thereof. A preferred class of derivatives is N-1- or N-6-carboxyalkyl-2-oxo-3-hydroxy-LSD derivatives having the following chemical structure:

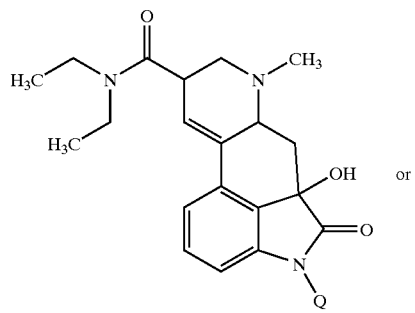

-continued

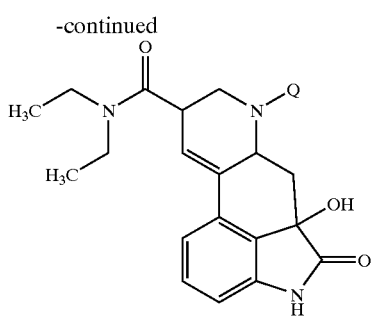

where Q is —$L^1$—G, $L^1$ is a linker containing at least one carbon atom, and G is selected from the group consisting of peptides, proteins, protein fragments, and immunogenic carriers. $L^1$ is preferably selected from the group consisting of $C_1$–$C_{20}$ hydrocarbon chains, containing zero to ten heteroatoms selected from the group consisting of N, O, and S.

The N-1-carboxyalkyl derivatives of 2-oxo-3-hydroxy-LSD can be prepared by derivatizing LSD to form an N-1-alkylcarboxyalkyl derivative, as in Example 1 below and U.S. Pat. No. 5,843,682. The derivatized LSD is then oxidized to N-1-alkylcarboxyalkyl-2-oxo-3-hydroxy-LSD. Hydrolysis of the alkylcarboxyalkyl ester yields N-1-carboxyalkyl 2-oxo-3-hydroxy-LSD. The latter derivative can be conjugated to amino groups on immunogenic carrier proteins to yield immunogens directly. This can be accomplished by preparation of active esters such as N-hydroxysuccinimide (NHS) esters, or by activation of the carboxylic acid group with 2-(1H-benzotriazole-1-yl)-1,1,3,3-tetramethyluronium hexafluorophosphate (HBTU) or by carbodiimides such as dicyclohexylcarbodiimide (DCC) or diisopropylcarbodiimide (DIC), followed by reaction with amino groups on the carrier protein. Alternatively, N-1-carboxyalkyl 2-oxo-3-hydroxy-LSD can be conjugated to amino groups on linkers, i.e., maleimidoalkylamines, to yield adducts suitable for conjugation to thiol groups of enzyme donor polypeptides, immunogenic carrier proteins or labeling groups.

In preparing immunogen, enzyme, or enzyme donor conjugates, a maleimide adduct can first be formed with an aminoalkyl-maleimide derivative. These aminoalkyl-maleimide derivatives are synthesized by the methods of Huber as described in PCT publication WO 90/15798 (Dec. 27, 1990). The maleimide adducts are reacted with thiol groups on the immunogen, enzyme or enzyme donor to give thioether-linked conjugates.

In a preferred approach, a thiol-containing carrier poly (amino acid) or other substance having immunogenic properties is coupled to the maleimide hapten. Although thiolated keyhole limpet hemocyanin (KLH) is an especially preferred antigenic poly(amino acid), or carrier protein, it should be understood that various protein carriers may be employed, including albumins, serum proteins, e.g., globulins, ocular lens proteins, lipoproteins and the like. Illustrative protein carriers include, but are not limited to, bovine serum albumin, egg ovalbumin, bovine gammaglobulin, thyroxine binding globulin, and viral core particles. Alternatively, synthetic poly(amino acids) having a sufficient number of available sulfhydryl groups such as cysteine may be employed, as may other synthetic or natural polymeric materials bearing reactive functional groups. In particular, carbohydrates, yeasts, or polysaccharides may be conjugated to the hapten to produce an immunogen.

Laboratory methods for producing polyclonal antibodies and monoclonal antibodies, as well as deducing their corresponding nucleic acid sequences, are known in the art, see *Handbook of Experimental Immunology* (D. M. Weir & C. C. Blackwell, eds.); *Current Protocols in Immunology* (J. E. Coligan et al., eds., 1991); David Wild, ed., *The Immunoassay Handbook* (Stockton Press NY, 1994); and R. Masseyeff, W. H. Albert, and N. A. Staines, eds., *Methods of Immunological Analysis* (Weinheim: VCH Verlags gesellschaft mbH, 1993).

Polyclonal antibodies of this invention are raised by administration of the immunogenic conjugate to an animal host, usually mixed with an adjuvant. Any animal host which produces antibodies can be used. The animal is preferably a vertebrate, more preferably a manual. The immunogen is conveniently prepared for injection by rehydrating lyophilized immunogen to form a solution or suspension. Preferred adjuvants are water-in-oil immersions, particularly Freund's complete adjuvant for the first administration, and Freund's incomplete adjuvant for booster doses. The preparation is typically administered in a variety of sites, and typically in two or more doses over a course of at least 4 weeks. Serum is harvested and tested for the presence of specific antibody using a hapten-protein conjugate or other competitive binding compound for the analyte in a standard immunoassay or precipitation reaction.

Preparation of monoclonal antibodies using the aforementioned immunogen is generally in keeping with established and conventional techniques. While mouse is a preferred host for immunization, it is contemplated that any animal subject that produces antibodies, including humans or antibody producing cells therefrom can be manipulated according to the processes of this invention to serve as the basis for production of mammalian, including human, hybridoma cell lines. For hybridoma technology, the reader is referred generally to Harrow & Lane (1988), U.S. Pat. Nos. 4,491,632, 4,472,500, and 4,444,887, and *Methods in Enzymology*, 73B:3 (1981). The most common way to produce monoclonal antibodies is to immortalize and clone a splenocyte or other antibody-producing cell recovered from an immunized animal. The clone is immortalized by a procedure such as fusion with a non-producing myeloma, by transfecting with Epstein Barr Virus, or transforming with oncogenic DNA. Available myeloma lines, include but are not limited to X63-Ag8.653 and those from the Salk Institute, Cell Distribution Center, San Diego, Calif., USA, may be used in the hybridization. The treated cells are cloned and cultured, and clones that produce antibody of the desired specificity are selected. A supply of monoclonal antibody from the selected clone can then be purified from a large volume of culture supernatant, or from the ascites fluid of suitably prepared host animals injected with the clone. The antibody can be tested for activity as raw supernatant or ascites, and is optionally purified using standard biochemical preparation techniques such as ammonium sulfate precipitation, ion exchange chromatography, and gel filtration chromatography.

Alternative methods for obtaining monoclonal antibodies involve contacting an immunocompetent cell or viral particle with a desired analyte or an analyte-protein complex in vitro. In this context, "immunocompetent" means that the cell or particle is capable of expressing an antibody specific for the antigen without further genetic rearrangement, and can be selected from a cell mixture by presentation of the antigen. Immunocompetent eukaryotic cells can be harvested from an immunized mammalian donor, or they can be harvested from an unimmunized donor and prestimulated in vitro by culturing in the presence of immunogen and immunostimulatory growth factors. Cells of the desired specificity can be selected by contacting with the immmunogen under culture conditions that result in proliferation of specific clones but not non-specific clones. Immunocompetent phage can be constructed to express immunoglobulin variable region segments on their surface. See Marks et al., New Engl. J. Med. 335:730, 1996; international patent applications WO 94/13804, WO 92/01047, and WO 90/02809; U.S. Pat. Nos. 5,871,907, 5,858,657, and 5,733,743; and McGuinness et al., Nature Biotechnol. 14:1149, 1996. Phage of the desired specificity can be selected, for example, by adherence to a hapten-protein complex attached to a solid phase, and then amplified in *E. coli*.

Antibodies exhibiting specificity for 2-oxo-3-hydroxy-LSD and its derivatives can be identified by any suitable screening techniques, which generally employ the immunizing hapten as the detecting reagent in an immunoassay. One such method as illustrated below is to conduct test immunoassays using corresponding competitive binding compounds, such as a 2-oxo-3-hydroxy-LSD enzyme or enzyme donor conjugate made using an activated form of 2-oxo-3-hydroxy-LSD. An exemplary activated 2-oxo-3-hydroxy-LSD derivative has the chemical formula:

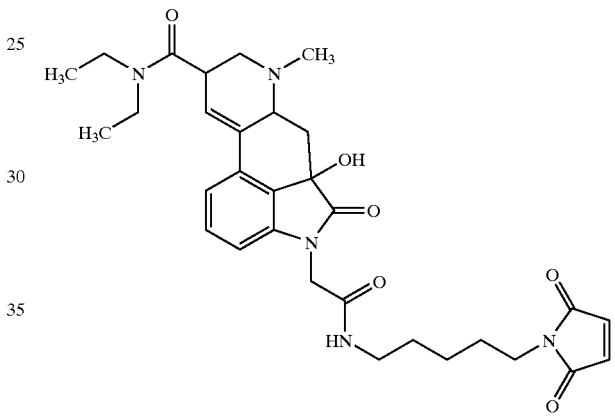

The ability of an antibody to specifically recognize 2-oxo-3-hydroxy-LSD or its derivatives can also be measured directly in the screening assay using the metabolite or its derivative as the test analyte. Derivatives of 2-oxo-3-hydroxy-LSD can be prepared according to the exemplary methods disclosed herein or any other methods known in the art. The recommended conjugation position is away from the alkyl amide group, such as the N-1 or 6 position. The N-1 position is preferred.

Upon identification of samples containing either polyclonal or monoclonal antibodies that exhibit the desired binding specificity, undesired activities, if present, can be removed from the sample by, for example, running the preparation over adsorbents made of the immunogen attached to a solid phase and eluting or releasing the desired antibodies off the immunogen. The specific antibody activity can be further purified by such techniques as protein A chromatography, ammonium sulfate precipitation, ion exchange chromatography, or high-performance liquid chromatography. In one aspect, the antibodies of the invention are specific for 2-oxo-3-hydroxy-LSD; in another aspect, the antibodies are specific for both 2-oxo-3-hydroxy-LSD and the parent drug LSD.

The antibodies of this invention can also be conjugated to a detectable agent. The complex is useful to detect 2-oxo-3-hydroxy-LSD and its derivatives to which the antibody specifically binds in a sample, using standard immunochemical techniques or methods disclosed herein. There are many different labels and methods of labeling known to those of ordinary skill in the art. Examples of the types of labels which can be used in the present invention include radioisotopes, enzymes, colloidal metals, fluorescent compounds fluorescent quench label, bioluminescent compounds, and chemiluminescent compounds. A preferred enzyme-based label is an enzyme donor of β-galactosidase. Those of ordinary skill in the art will know of other suitable labels for binding to the antibody, or will be able to ascertain such, using routine experimentation. Furthermore, the binding of these labels to the antibody of the invention can be done using standard techniques common to those of ordinary skill in the art.

Antibodies also can be "insolubilized" by attaching them to a vessel wall, to a particulate, or to a large molecular weight carrier that can be kept in suspension but is removable by physicochemical means, such as centrifugation or microfiltration. Antibodies can also be insolubilized on test strips, cartridge devices, and lateral flow immunoassay devices. The attachment need not be covalent, but is at least of sufficient permanence to withstand any separation techniques (including washes) that are part of the assay procedure. Suitable particulate materials include agarose, polystyrene, cellulose, polyacrylamide, latex particles, magnetic particles, and fixed red cells. Suitable commercially available matrices include Sepharose® (Pharmacia), Poros® resins (Boehringer Mannheim Biochemicals, Indianapolis), Actigel Superflow™ resins (Sterogene Bioseparations Inc., Carlsbad Calif.), and Dynabeads™ (Dynal Inc., Lake Success, N.Y.). The choice is not critical, and will generally depend on such features as stability, capacity, accessibility of the coupled antibody, flow rate (or the ability to disperse the resin in the reaction mixture), and ease of separation.

The antibodies embodied in the present invention can be used as detecting or neutralizing antibodies in an immunoassay for detecting and/or confirming the presence of 2-oxo-3-hydroxy-LSD or its derivative present in a test sample. Detecting antibodies for use in enzyme complementation assays in the CEDIA® series are selected on the basis of specificity for the analyte, and also on the basis of three other criteria. One, referred to as "inhibition," relates to how well the antibody binds the enzyme-donor conjugate and blocks enzyme formation. Sufficient inhibition (preferably at least about 70%) is needed in order to provide an adequate signal. A second criterion is the titer of the antibody required to obtain the desired level of inhibition. Inhibition at lower antibody levels is preferred. A third criterion, referred to as "modulation", relates to how well the sample analyte is able to compete with the conjugate for enzyme binding. Modulation is calculated as the difference in enzyme rate between a sample having the analyte at a target concentration (moderately chosen within the intended working range) and a sample having no analyte, divided by the rate at the target concentration. Better modulation correlates with better assay sensitivity. Detecting antibodies for other types of assays are selected by criteria appropriate to provide the desired sensitivity and specificity through the working range.

Neutralizing antibodies are selected on the basis of criteria necessary for their use in the intended assay system. Neutralizing antibodies that are maintained in the reaction mixture during the detection of any uncomplexed interfering substance, such as in a bidirectional type confirmatory assay, must not react with the other reagents in the mixture and give a false signal. In particular, they must not be able to take the place of detecting antibody in binding to any hapten derivative involved in signal generation. Thus, neutralizing antibodies are selected that do not have this activity, either by direct negative selection for the unwanted binding characteristic, or by negative selection in an assay mixture according to the immunoassay method in the absence of detecting antibody. If the detecting antibody is raised against a conjugate of 2-oxo-3-hydroxy-LSD derivatized at a position in the indole ring, then the neutralizing antibody should be raised against a conjugate of 2-oxo-3-hydroxy-LSD derivatized at a position other than in the indole ring. Such a position can be, for example, the 6-position of 2-oxo-3-hydroxy-norLSD.

Immunoassay for 2-oxo-3-hydroxy-LSD

The assay procedure entails combining the sample with the antibody specific for the analyte, 2-oxo-3-hydroxy-LSD or its derivative, under conditions that permit the formation of a stable complex between the analyte and the antibody. A "stable complex" is a complex that persists at least as long as it takes the presence of the complex to be measured by the intended method. In one immunoassay method of this invention, this is followed by detecting any analyte-antibody complex that is formed. The detecting antibody binds a labeled competitive binding compound (typically a labeled form of 2-oxo-3-hydroxy-LSD or LSD, or their derivatives), in a manner that is inhibitable by the metabolite 2-oxo-3-hydroxy-LSD and optionally also by the parent LSD compound. In this embodiment, the substance to be tested intercedes between the labeled competitive binding compound, reducing the amount of labeled compound bound to antibody in a competition reaction.

Another type of assay is a confirmation or confirmatory assay that can be employed for distinguishing between the analyte, 2-oxo-3-hydroxy-LSD, and an interfering substance possibly present in the test sample. Unlike previous strategies that have been principally oriented at either improving the specificity of the detecting antibody, or neutralizing the effect of the interfering substance in the sample, the confirmatory assay of the present invention aims at removing or neutralizing the true analyte, and re-testing the sample for the analyte. Specifically, the confirmatory assay involves conducting an immunoassay to determine the amount of analyte and/or interfering substance in the sample (the direct test); treating the same sample or a duplicate of the sample with a neutralizing antibody in an amount sufficient to remove or inactivate the analyte but not the potential interfering substance; and conducting an immunoassay to determine the amount of apparent analyte in the treated sample (the confirmatory test). Samples giving a positive reaction in a direct immunoassay test are treated with a neutralizing antibody that inhibits reactivity of the true analyte, but not the interfering substance. Thus, samples giving a positive reaction in the direct test but decreased reaction in the confirmation test are marked as containing the true analyte. Samples giving a positive reaction of roughly equivalent magnitude in both the direct and confirmation test are marked as containing an interfering substance. The confirmatory assay can be an adsorption type or a bidirectional antibody type assay.

In an adsorption-type confirmation assay, the sample is treated with a particular amount of neutralizing antibody that is sufficient to remove the analyte, namely 2-oxo-3-hydroxy-LSD, but not all of a particular interfering substance from the sample, or otherwise prevent its binding to the detecting antibody.

The neutralizing antibody preferentially binds the analyte in comparison with the interfering substance, meaning that it binds 2-oxo-3-hydroxy-LSD about 5 times better. preferably at least about 25, 100, or even about 1000 times better, compared with the potential interfering substance. Preferential inhibition may occur because the affinity of the neutralizing antibody for 2-oxo-3-hydroxy-LSD is at least 10 times and preferably 100 or 1000 times higher than it is for the potential interfering substance.

The neutralizing antibody can optionally be different from the detecting antibody. However, it has been discovered that this is not critical to the practice of adsorption type confirmatory assay in a number of its embodiments. The assay can be performed by using the same antibody for both neutralizing and detecting. The key is to provide enough antibody at the neutralizing step to remove or inactivate the analyte, but not enough to remove or inactivate the interfering material. The technique takes advantage of the following two features: first, the specificity of the antibody, as indicated in the preceding section; and second, the fact that the interfering substance must be present in large molar excess in order to have given a positive reaction in the direct test. One of skill in the art will also appreciate that it is not necessary for the neutralizing antibody to remove or inactivate absolutely all of the analyte, providing that it removes a greater proportion of analyte than interfering substance. In this way, thresholds can be set in the confirmatory part of the test that can be recorded as negative (confirming the presence of analyte) or positive (indicating the presence of interfering substance).

The neutralizing antibody can act to prevent the analyte, 2-oxo-3-hydroxy-LSD, from reacting with the detecting antibody in the detection phase of the confirmatory test by several different mechanisms. In one mechanism, the neutralizing antibody simply binds the analyte at the same epitope (in a similar or dissimilar orientation) as the detecting antibody. For example, where the detecting antibody is conjugated to the labeling system, such as in the enzyme complementation assay described in U.S. Pat. No. 5,212,064, the neutralizing antibody could be the same Fab fragment (or the whole antibody equivalent) in an unconjugated form. The neutralizing antibody prevents binding of the analyte to the detecting antibody conjugate. In another example, the neutralizing antibody recognizes the analyte from a different orientation from the detecting antibody, but again prevents binding of the analyte to the detecting antibody conjugate.

In some cases, the neutralizing antibody is used to pretreat the sample and remove the true analyte in preference to the interfering substance. Then the sample is tested using a detection antibody and competitive binding compound in a similar fashion to the direct test. Any type of immunoadsorption can be used. Typically, the neutralizing antibody is "insolubilized", which means that it is attached to an insoluble polymer or bead made of a suitable inert material, such as polystyrene, polyacrylamide, cellulose, and the like, or the side of a vessel wall through which the sample is passed or preincubated. An affinity separation step can be performed by column chromatography or filtration. However, elaborate separation procedures are generally not necessary. A convenient procedure is to simply add an affinity matrix into the sample, keep in suspension for sufficient time to adsorb the analyte, and then allow it to settle to the bottom of the reaction vessel. The supernatant can then be assayed for interfering substance.

In a variation of this approach, the neutralizing antibody is not attached directly to a solid surface, but insolubilized after it is added to the sample. A secondary insolubilized capture antibody or binding compound can be used for this purpose. For example, if the neutralizing antibody is a mouse anti-analyte antibody, then the capture antibody can be a polyclonal rabbit anti-mouse immunoglobulin reagent bound to a solid phase. In another example, the neutralizing antibody can be provided with a suitable capture ligand, such as fluorescein or biotin. Following incubation with the sample, the antibody (along with bound analyte) is removed using a receptor with the matching specificity: respectively anti-fluorescein antibody, or avidin. In a further variation of this approach, the primary antibody or the capture antibody is linked to a ferromagnetic particle, which is subsequently removed from the solution (along with the analyte) using a magnetic field.

Whatever the mechanism for removing or inactivating the true analyte, the amount of neutralizing antibody is adjusted so as to be sufficient to remove the majority of the analyte but only a small fraction of the interfering substance. Where the neutralizing antibody is linked to a particulate, it can be diluted as needed by adding additional particulate which has not been activated or which is linked to an alternative, inactive molecule such as bovine albumin. This permits an appropriate amount of antibody to be provided in an easily handled amount of particulate.

A bidirectional antibody type confirmatory assay is an assay in which the neutralizing antibody and the detecting antibody recognize the analyte, 2-oxo-3-hydroxy-LSD from different orientations. Depending on the nature of the assay, this can provide either of the following advantages: (1) Since the neutralizing antibody recognizes the analyte from a different direction, the chances that it will have. the same cross-reactivity profile as the detecting antibody are decreased. An interfering substance with unrelated pharmacological activity that fortuitously resembles the analyte on one side is unlikely to resemble the analyte to the same extent on the opposite side. (2) Where desirable, neutralizing antibodies can be obtained that can be added directly to the reaction mixture without affecting the detection system. In this embodiment, no preadsorption with the neutralizing antibody is required.

The usual reagents for conducting the direct test for analyte are a detecting antibody specific for the analyte, 2-oxo-3-hydroxy-LSD, and a competitive binding compound which is typically a hapten, such as a 2-oxo-3-hydroxy-LSD derivative. The detecting antibody binds the hapten derivative in a manner that is specifically inhibitable by the analyte. The hapten derivative is typically a modified form of the analyte or a closely related chemical structure, adapted so as to provide a signal detection system. In an assay which comprises measuring fluorescence emission or fluorescence polarization, the hapten derivative is a fluorescent hapten or a fluorescent quench hapten, typically a chemically modified form of the analyte in which the fluorescent or fluorescent quench group is adapted onto one end.

In certain types of enzyme immunoassays, the hapten derivative is a conjugate in which the hapten is linked to an enzyme, either through a covalent bond or through a bridging structure, such as may be formed using a cross-linking agent, or using a hapten chemically modified with the bridging structure with a protein-linking group on the far end. In other types of enzyme immunoassays, the hapten derivative is a conjugate in which the hapten is linked to an enzyme fragment which complements with a second enzyme fragment to form an active enzyme complex. In certain types of assays, the hapten derivative is a conjugate in which the hapten is linked to an inert substance, such as a large protein, a polymer (such as polystyrene, polyacrylamide, latex, or a high molecular weight carbohydrate), a particulate, or the surface of the reaction vessel. The hapten can also be conjugated to members of the group consisting of fluorescent, chemiluminescent, phosphorescent, and chromophoric compounds, a fluorescence quenching group, a radioisotopically labeled group, an electrochemically active group, an electrochemiluminescent group, a group that undergoes a change in fluorescence, phosphorescence, chemiluminescence or electrochemical property upon binding, peptides, proteins, protein fragments, immunogenic carriers, enzymes, enzyme donors, enzyme inhibitors, enzyme substrates, enzyme cofactors, enzyme prosthetic groups, solid particles, gold particles, antibodies, and nucleic acids. The hapten can also be immobilized on test strips, cartridge devices, and lateral flow immunoassay devices.

In any of these systems, the direct test is conducted by preparing a reaction mixture comprising the sample, the detecting antibody, and the competitive binding compound. The test is completed by measuring the amount of the complex formed between the detecting antibody and the competitive binding compound, in competition with the analyte from the sample. Depending on the detection means used, the amount of complex may correlate positively or inversely with the amount of analyte (or cross-reacting substance) in the sample.

The neutralization test is conducted in a similar fashion, using a detecting antibody for the analyte, and a competitive binding compound which is typically a hapten derivative. There is no absolute requirement that the detecting antibody, the competitive binding compound, or even the detection means be the same as in the direct test, but it is usually most convenient and most accurate if the same reagents are used in the same concentration. The neutralization test additionally involves a neutralizing antibody, which has the function of preventing a proportion of the true analyte from reacting with the detection antibody, thereby reducing the assay signal.

The neutralization test is typically conducted by preparing a reaction mixture comprising the sample, the detecting antibody, the neutralizing antibody, and the competitive binding compound or hapten derivative, and then measuring the formation of reaction complexes as in the direct test. In certain embodiments of the assay, the neutralizing antibody is preincubated with the sample in which the analyte is to be measured. Usually, however, this is not required, and it is sufficient to add the sample to a reaction mixture containing the detecting and neutralizing antibody together. In certain embodiments of the assay, the hapten conjugate reagent is added after the antibodies are in equilibrium with any analyte in the sample. More generally, the reagents may be combined in any order, depending on the kinetic parameters of the reaction system. The neutralization test is completed by measuring the amount of the complex formed between the detecting antibody and the competitive binding compound, and correlating the result with the degree of neutralization of the substance in the original sample. Successful neutralization of a sample testing positive in the direct test indicates the presence of true analyte.

Characteristics of the reagents are as follows. The hapten derivative "preferentially" binds the detecting antibody in comparison with the neutralizing antibody. This means that under assay conditions and in the absence of analyte, the proportion of hapten derivative bound to detecting antibody is at least about 10 times higher, preferably at least about 100 or 1000 times higher than that the proportion of hapten derivative bound to neutralizing antibody. Typically, the affinity of the detecting antibody for the hapten derivative is at least 10 times and preferably 100 or 1000 times higher than that of the neutralizing antibody. The affinity of the detecting antibody for the hapten derivative will generally have an affinity of at least about $10^8$ $M^{-1}$, with affinities of at least about $10^9$ $M^{-1}$, $10^{10}$ $M^{-1}$, and $10^{10}$ $M^{-1}$ being increasingly more preferred. The binding of the neutralizing antibody to the hapten derivative will generally have an affinity of no more than about $10^7$ $M^{-1}$, with affinities of no more than about $10^6$ $M^{-1}$ or $10^5$ $M^{-1}$ being increasingly more preferred.

Binding of the neutralizing antibody to the analyte inhibits binding of the analyte to the detecting antibody. This means that in an assay conducted in the working range in the presence of the neutralizing antibody, the binding of the analyte to the detecting antibody and subsequent specific signal generation is reduced by at least about 2-fold, and preferably 5-fold, 25-fold, or 100-fold in order of increasing preference. Higher degrees of inhibition can be obtained by using a neutralizing antibody that has a higher affinity for the analyte than does the detecting antibody. Another option is to preincubate the neutralizing antibody with the sample before adding the detecting antibody in a non-equilibrium situation. More typically, the amount of neutralizing antibody in the reaction mixture is in excess (preferably 10 fold or even 100 fold higher), thereby increasing analyte binding to the detecting antibody by mass action.

In certain embodiments of this type of assay, the neutralizing antibody also "preferentially" inhibits binding of the analyte to the detecting antibody, in comparison with a potential interfering substance. This means that in a reaction mixture containing both analyte and interfering substance within the working range of the assay, the proportion of analyte bound to the neutralizing antibody is at least about 5 times higher, preferably at least about 25, 100, or 1000 times higher than that the proportion of interfering substance bound to neutralizing antibody. Preferential inhibition may occur because the affinity of the neutralizing antibody for the analyte is at least 10 times and preferably 100 or 1000 times higher than it is for the potential interfering substance.

Any pair of detecting and neutralizing antibodies having the functional properties described in the foregoing discussion fall within the scope of the invention. Most conveniently, detecting and neutralizing antibodies are obtained by using immunogen or antibody screening or purifying reagents using different hapten-carrier conjugates, in which a chemical analog of the analyte is linked to the carrier in different orientations. The conjugate used to raise or select the detecting antibody is usually one in which the hapten is linked to the carrier in a position that is identical or nearby the position in which the hapten is linked or modified in the hapten derivative used in the assay. The conjugate used to raise or select the neutralizing antibody is selected to enhance the likelihood that the antibody will not react with the hapten derivative used in the assay, in accordance with the properties described above. Thus, the conjugate presents the hapten so as to elicit antibodies that will be sterically inhibited from reacting with the hapten derivative of the assay (in the case of an enzyme conjugate), or will be faced with the signaling moiety of the hapten derivative (in the case of a fluorescently modified analog) and be unlikely to cross-react. Typically, but not necessarily, the presentation of the hapten used to raise the detecting and neutralizing antibodies will be from different positions (e.g., N-1 and N-6) of the molecule.

Assays suitable for use or modification in this invention include both qualitative and quantitative assays. Typical quantitative methods involve mixing the analyte with a pre-determined amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte establish the assay result. Unless otherwise required, "measuring" refers both to qualitative and quantitative determination.

Immunoassays for measuring 2-oxo-3-hydroxy-LSD or its derivatives include both separation-based and homogeneous assays. In separation based assays, the detecting of the complex involves a process wherein the complex formed is physically separated from either unreacted analyte, unreacted antibody, or both. See, e.g., U.S. Pat. No. 3,646,346. The complex can be first formed in the fluid phase, and then subsequently captured by a solid phase reagent or separated on the basis of an altered physical or chemical property, such as by gel filtration or precipitation. Alternatively, one of the reagents can be attached to a solid phase before contacting with other reagents, and then the complex can be recovered by washing the solid phase free of unreacted reagents. Separation-based assays typically involve use of a labeled analog or antibody to facilitate detection or quantitation of the complex. Suitable labels are radioisotopes such as $^{125}$I, enzymes such as peroxidase and β-galactosidase, and fluorescent labels such as fluorescein isothiocyanate. The separation step involves removing labeled reagent present in complex form from unreacted labeled reagent. The amount of label in the complex can be measured directly or inferred from the amount left unreacted. By way of example, a sample can be tested for 2-oxo-3-hydroxy-LSD by mixing with labeled anti-2-oxo-3-hydroxy-LSD antibody and solid-phase 2-oxo-3-hydroxy-LSD. After washing, the amount of label bound to the solid phase inversely correlates with the amount of 2-oxo-3-hydroxy-LSD in the sample.

In homogeneous assays, the complex is typically not separated from unreacted reaction components, but instead the presence of the complex is detected by a property which at least one of the reactants acquires or loses as a result of being incorporated into the complex. Homogeneous assays known in the art include systems involving fluorochrome and fluorochrome quenching pairs on different reagents (U.S. Pat. Nos. 3,996,345, 4,161,515, 4,256,834, and 4,264,968); enzyme and enzyme inhibitor pairs on different reagents (U.S. Pat. Nos. 4,208,479 and 4,233,401); chromophore and chromophore modifier pairs on different reagents (U.S. Pat. No. 4,208,479); and latex agglutination assays (U.S. Pat. Nos. 3,088,875, 3,551,555, 4,205,954, and 4,351,824).

Assays of this invention include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. For small molecule drugs, competition assays are more common. Competition assays involve a system in which the analyte to be measured competes with an analog of the analyte for binding to another reagent, such as an antibody. In the context of immunoassay, a "competitive binding compound" refers to a compound that is able to compete with the analyte to be measured in the sample for binding to the detecting antibody. A preferred competitive binding compound is a derivative of LSD or derivative of 2-oxo-3-hydroxy-LSD metabolite. Competitive binding compounds are identified functionally, and include radioisotope conjugates, enzyme conjugates, and other protein complexes, and structurally similar chemical analogs. CEDIA® is an example of a competition assay.

Homogeneous assay methods of this invention are exemplified by enzyme complementation assays, exemplified by the cloned enzyme donor immunoassay system described in U.S. Pat. No. 4,708,929. Related reagents and methods are taught in U.S. Pat. Nos. 5,254,577; 5,444,161; 5,464,747; and 5,514,560. Cloned enzyme donor immunoassays are available commercially under the registered trademark CEDIA®. Typically, a cloned enzyme donor immunoassay involves combining the sample with a specific detecting antibody; an enzyme donor polypeptide conjugate; an enzyme acceptor polypeptide (wherein the enzyme acceptor polypeptide is capable of forming with said enzyme donor polypeptide conjugate an active enzyme complex in the absence of an antibody to the analyte), and a substrate capable of being transformed by the active enzyme complex into a product. The amount of product is then measured, usually as a function of time.

Preferred enzyme-donor and enzyme-acceptor polypeptides are based on the enzyme β-galactosidase polypeptide. A "β-galactosidase polypeptide" is a polypeptide identifiable on the basis of its amino acid sequence or enzymatic activity as being developed from an enzyme with β-galactosidase activity, and includes naturally occurring β-galactosidase, fragments, deletion mutants, fusion proteins, mutants, and other variants. Particular β-galactosidase polypeptides are described in the aforementioned U.S. Patent applications pertaining to cloned enzyme donor immunoassays.

β-galactosidase enzyme acceptors are preferably produced by a deletion mutant of the β-galactosidase gene. EA22, one of the preferred acceptors, has a deletion of amino acid residues 13–40. Other enzyme acceptor fragments of β-galactosidase include EA5, EA11, EA14, EA17, EA18, EA20, EA23 and EA24. The distal end of the deleted segment normally falls between amino acid positions 26 and 54 of the β-galactosidase sequence. In EA22, the distal end of the deletion segment is amino acid 40.

A particularly preferred beta-galactosidase enzyme donor is ED28. ED28 is a 90 amino acid peptide containing residues 6–45 of beta-galactosidase, with cysteines at positions 1 and 46 (relative to the numbering of the original beta-galactosidase fragment). The sequence of ED28 is (SEQ ID NO:1) Met-Asp-Pro-Ser-Gly-Asn-Pro-Tyr-Gly-Ile-Asp-Pro-Thr-Gin-Ser-Ser-Pro-Gly-Asn-Ile-Asp-Pro-Cys-Ala-Ser-Ser-Asn-Ser-Leu-Ala-Val-Val-Leu-Gln-Arg-Arg-Asp-Trp-Glu-Asn-Pro-Gly-Val-Thr-Gln-Leu-Asn-Arg-Leu-Ala-Ala-His-Pro-Pro-Phe-Ala-Ser-Trp-Arg-Asn-Ser-Glu-Glu-Ala-Arg-Thr-Asp-Cys-Pro-Ser-Gln-Gln-Leu-Ala-Gln-Pro-Glu-Trp-Gly-Leu-Glu-Ser-Arg-Ser-Ala-Gly-Met-Pro-Leu-Glu; see also European Patent Application No. 90308937.3 and U.S. Pat. Nos. 4,708,929, 5,444,161, and 5,763,196. The two cysteine residues can be used for exact and reproducible placement of sulfhydryl-reactive adducts of a chemical hapten, as illustrated in the examples.

Preferred substrates for use in immunoassays based on β-galactosidase include those described in U.S. Pat. Nos. 5,032,503; 5,254,677; 5,444,161 and 5,514,560. Amongst the preferred substrates is chlorophenol β-D-red galactopyranoside (CPRG).

CEDIA® type homogeneous assays for small molecule analytes are often formulated such that an analog of the analyte is attached to the enzyme donor near a site involved in recombination of the donor and acceptor. For example, assays for procainamide and N-acetylprocainamide (NAPA)

are described in U.S. Pat. Nos. 5,439,798 and 5,525,474. Binding of an antibody in the solution to the analog in the conjugate inhibits recombination into an active enzyme complex. Thus, the presence of analyte in the sample is positively correlated with enzyme activity. U.S. Pat. No. 5,212,064 describes a different approach; in which the antibody fragment is conjugated to the enzyme donor, and the analog is conjugated to a macromolecule or insoluble particle. Binding of the enzyme donor to the analog conjugate via the antibody inhibits recombination with the enzyme acceptor. Analyte in the sample competes with the analog conjugate, freeing up the enzyme donor for recombination with the acceptor. Again, the presence of analyte in the sample is positively correlated with enzyme activity.

Other assay systems of particular interest are enzyme immunoassays based on glucose-6-phosphate dehydrogenase (G6PD). Examples are provided in International Patent Application WO 94/24559 and EP Patent Application 487, 301-A. A homogeneous assay can be performed, in which G6PD is conjugated with an analog of the analyte in a position where binding of an antibody to the analog inhibits G6PD activity. If the test sample contains the analyte of interest, it competitively binds the antibody, which is then prevented from binding the G6PD. Thus, enzymatic activity correlates positively with the presence of analyte in the sample.

The assay methods of this invention can be carried out manually, or on automated equipment. Devices suitable for confirmatory assays generating an enzymatic signal include analyzers in the Beckman Synchron™ series, Olympus analyzers (AU800, AU5000, AU 5200), Roche COBAS® analyzers, and devices in the Boehringer Mannheim/Hitachi series. Analyzers suitable for performing bidirectional antibody type confirmation assays for 2-oxo-3-hydroxy-LSD, similar to those illustrated in Example 4, include BM/Hitachi models 704, 717, 747, 902, 911, 912, 914, and 917. Analyzers suitable for performing adsorption type confirmation assays for LSD include BM/Hitachi models 902, 911, 912, and 717.

For the purposes of screening for prior LSD exposure, an assay capable of detecting both LSD and 2-oxo-3-hydroxy-LSD metabolites can be used; the ability to detect the metabolites having the effect of extending the window of detection. For legal purposes, once a positive screening test result is obtained, it may be desirable to distinguish between LSD and 2-oxo-3-hydroxy-LSD in the sample. Options for distinguishing include immunoassays or immunoadsorptions using antibodies specific for only one of the two types of compounds, complex physicochemical techniques such as combinations of liquid or gas chromatography and mass spectrometry (LC/MS or GC/MS).

Reagent Sets and Kits

This invention includes various reagent sets, which are effective in performing an assay of this invention, or in adapting an assay for particular determination or purpose. Reagent sets may include any or all of the following in various combinations: an antibody specific for 2-oxo-3-hydroxy-LSD or a cocktail thereof that may either act as a detecting or a neutralizing antibody, a labeled competitive binding compound, other components of a signal generation system, buffers, or standards. For sets that include a plurality of reagents, it is not necessary that the reagents all be sold together or by the same distributor, so long as they have the desired functionality. It may be appropriate to distribute the reagents separately, for example, when the shelf life of one reagent is shorter than that of the rest of the system.

This invention also includes kits, in which one or more reagents are provided in suitable packaging. The reagents are optionally aliquoted so that they can be readily used in a clinical system. A kit will often contain written instructions for the performance of the assay method. This can be limited to a simple indication on the packaging that the ingredients are suitable for measuring the analyte of interest. Preferably, the written instructions will also indicate important steps and conditions for performing the tests, and data useful in interpreting the tests. For adsorption type confirmatory assays, the kit preferably contains an indication of the amount of neutralizing antibody to be added to each sample or the neutralizing antibody will be pre-aliquoted in the appropriate amount.

Further illustration of the development and use of reagents and assays according to this invention are provided in the Example section below. The examples are provided as a guide to a practitioner of ordinary skill in the art, and are not meant to be limiting in any way.

EXAMPLES

Example 1

Preparation of 2-oxo, 3-hydroxy LSD Metabolite Adducts, Immunogens, or Conjugates The preparation 2-oxo-3-hydroxy-LSD immunogens can be carried out according to the reaction scheme illustrated in FIG. 1 and the procedures detailed in the following sections.

Example 1A

Preparation of N-1-carboxymethyl-LSD (1-NCM-LSD)

The synthesis of the starting material, 1-NCM-LSD, used for preparing 2-oxo-3-hydroxy-LSD immunogens was carried out as follows.

Figure 2:
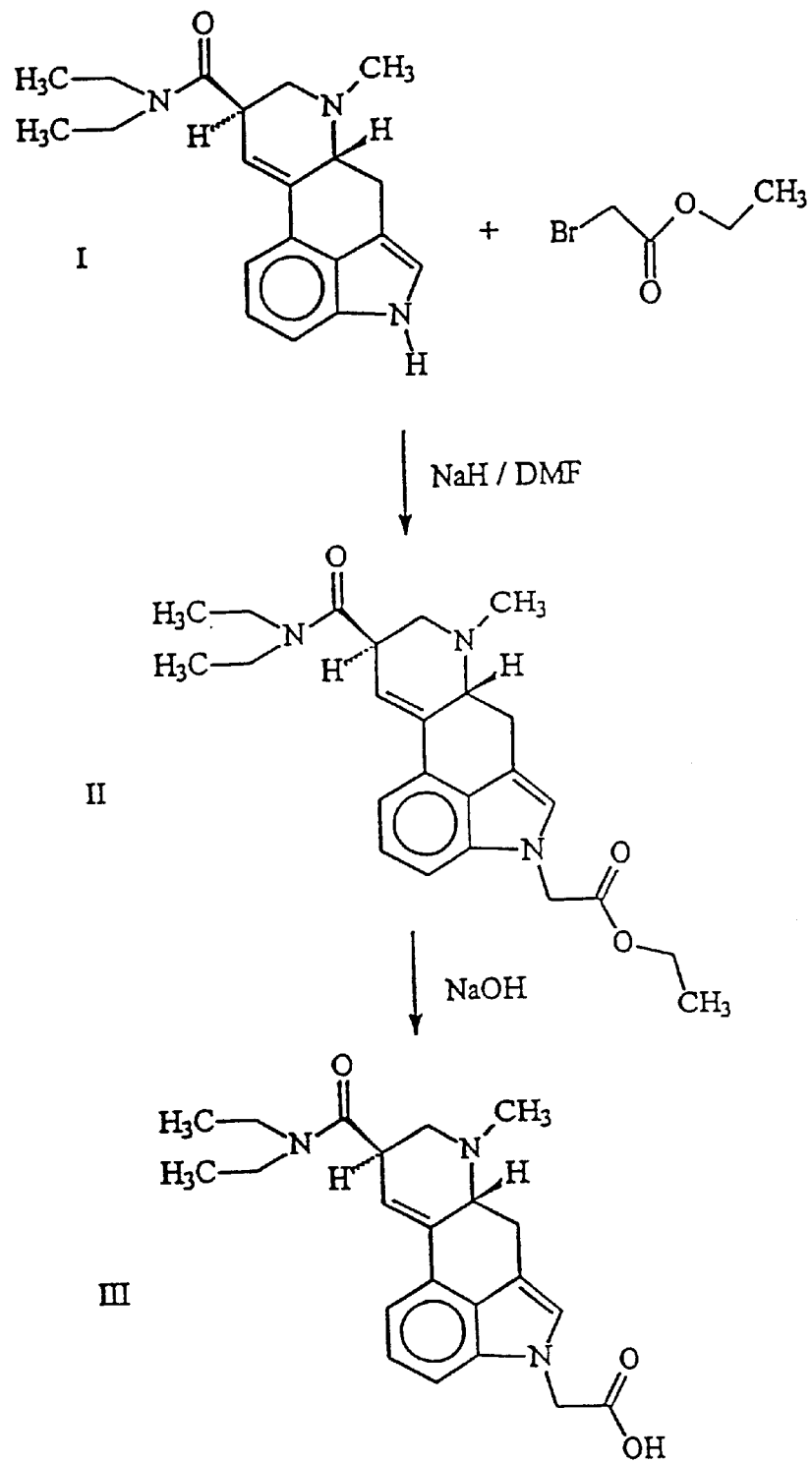
FIG. 2 illustrates a particular synthetic scheme for preparing N-1-carboxymethyl-LSD.

N-1-(ethyl-carboxymethyl)-LSD (formula II shown in FIG. 2) was prepared as a starting material by treating LSD (formula I) with a molar excess of sodium hydride followed by the addition of ethylbromoacetate. The ester formed was hydrolyzed to yield N-1-carboxymethyl-LSD (1-NCM-LSD, formula III). The synthetic scheme, described in detail below, is illustrated in FIG. 2.

Since LSD was found to be difficult and hazardous to weigh by transfer due to static charge effects, a method for reconstituting a total vial and weighing by subtraction was adopted. Working in a glove box which had been purged with nitrogen gas, 308 $\mu$mol sodium hydride was weighed directly into a tared 2.5 ml conical reaction vial. Dimethylformamide (DMF), 400 $\mu$l, was added to the reaction vial, along with a magnetic stir bar, open cap, and septum with TEFLON (synthetic resin polymer)-coated face. The vial was placed in a beaker containing crushed dry ice for approximately 10 min. DMF, 300 $\mu$l, was added to a tared, 50 mg vial of LSD, and the vial was capped and inverted several times until a complete solution was obtained. The LSD solution was transferred to a small culture tube (12×75 mm), capped and placed in the dry ice for approximately 10 min. The empty LSD vial was then rinsed with acetone, dried and weighed to obtain the net weight of LSD removed by subtraction, 50 mg (154 $\mu$mol). After removing the reaction vial from the dry ice and placing on a magnetic stir plate, the LSD solution was injected while vigorously stirring the sodium hydride suspension in the vial. Evolution of hydrogen gas and bright yellow coloration was noted. The suspension was allowed to warm with stirring for about 5 min, at which point the gas evolution had subsided.

Ethylbromoacetate, 17 μl (164 μmol), was then injected and stirred for approximately 2 minutes. After removing the vial from the glove box, a 1–2 μl aliquot was removed for HPLC analysis, and the vial was then placed in a −70° C. freezer while the HPLC was being run. The HPLC aliquot was diluted in a 12×75 mm culture tube with 20 μl acetonitrile and 20 μl of 0.1 M triethylamine acetate (TEA-Ac). The sample was injected on a C4 analytical column (Vydac) and the following program was run: 0–5 min, 100% 0.1 M TEA-Ac (pH 7); 5–55 min, 0–50% acetonitrile/0.1 M TEA-Ac; 55–60 min, 100% acetonitrile; 60–70 min, 100% 0.1 M TEA-Ac. The flow rate was 1 ml/min, with UV detection at 320 and 280 nm. The HPLC showed nearly complete conversion of LSD eluting around 30–32% acetonitrile to a major product eluting around 40–42% acetonitrile which showed a slight back shoulder. The N-6 quaternized side-product elutes right after LSD, i.e., 32–33% acetonitrile.

The product was isolated by preparative HPLC on a 2.2×25 cm C4 column using the following program: 0–10 min, 10% acetonitrile/0.1 M TEA-Ac; 10–60 min, 10–60% acetonitrile/0.1 M TEA-Ac; 60–65 min, 65% acetonitrile/0.1 M TEA-Ac; 65–75 min, 10% acetonitrile/0.1 M TEA-Ac. The flow rate was 8 ml/min. The load solution was prepared by diluting the cold reaction mixture with 1 ml 0.1 M TEA-Ac, filtering the resultant, slightly turbid solution through a 1 μm syringe filter, and injecting the clear filtrate, 1.8 ml, on a 2 ml loop. The desired product eluted toward the end of the gradient with a back shoulder. Fractions were collected manually over the major peak, taking care to change fractions at the back shoulder. This back shoulder corresponds to partially resolved N-1-(ethyl-carboxymethyl)-isoLSD, i.e. epimerized at the 8-position. Analytical HPLC was performed on the major fractions and those which were free of the isoLSD shoulder were pooled and lyophilized. The fraction was analyzed by 1H-NMR in acetonitrile-$d_3$ and identity confirmed by mass spectrometry (MS). The NMR spectrum of N-1-(ethyl-carboxymethyl)-LSD showed an absence of the LSD 1-position NH at 9.0 ppm. However, all other LSD resonances were seen at approximately the same position as in the parent drug. This strongly indicated that the 1-position was substituted. In addition, new resonances were noted for the carboxymethyl $CH_2$ (4.9 ppm, 2 proton singlet) and the ethyl ester ($CH_2$ at 4.2 ppm, 2 proton quartet, and $CH_3$ at 1.3 ppm, triplet overlapped with diethylamide resonances). The recovered yield was calculated by comparing UV/visible in acetonitrile/water (50:50) using MW=409.5 and $E_{max}$=5895 for the peak around 320 nm and found to be 30 mg.

N-1-(ethyl-carboxymethyl)-LSD starting material (28.5 mg, 70 μmol) was dissolved in 3.5 ml of ethanol and transferred to a small vial equipped with a septum/needle attached to an inert gas line and small stir bar. The reaction vial was purged with argon gas. Sodium hydroxide, 75 μl of a 1N solution, was then injected with stirring. The reaction was monitored using the analytical system described above for preparing the starting material. The product eluted at about 24–25% acetonitrile as a sharp peak. A small amount of isoLSD derivative side product was noted which appeared as a back shoulder on the major peak. The reaction was complete in approximately 2 hr. The reaction mixture was then neutralized by adding one equivalent of acetic acid and 1 ml of water, and the resulting solution was clear. The product was isolated and desalted by HPLC on a preparative C4 column using 20 mM TEA-Ac, pH 7, and acetonitrile according to the following program: 0–5 min, 0% acetonitrile/20 mM TEA-Ac; 5–55 min, 0–50% acetonitrile/ 20 mM TEA-Ac; 55–60 min, 100% acetonitrile. The flow rate was 8 ml/min. The major peak, which eluted around 28–29% acetonitrile, was collected and fractions changed on the back side of the peak to eliminate any shoulder for isoLSD derivative. The pooled fractions were lyophilized and re-lyophilized 2 times from water/acetonitrile 4:1 to get ride of the TEA-Ac and convert the product to a zwitterion. The product was analyzed by 1H NMR in a mixture of acetonitrile-$d_3$ and deuterium oxide. The ethyl ester resonances noted above were confirmed to absent in the NMR whereas the other resonances as noted above were intact. The product was also analyzed by MS and confirmed to have a molecular ion peak corresponding to the theory molecular weight (MW) of 381. The recovered yield was calculated by UV in acetonitrile-H20 as described above for the starting material using MW=381 and $E_{max}$=5895. The yield of 1-NCM-LSD was found to be around 20 mg.

Example 1B

Oxidation of 1-NCM-LSD

1-N-carboxymethylene-lysergic acid diethylamide (1-NCM-LSD) (5 mg, 13.1 μmoles) and tartaric acid (1.48 mg, 9.83 umoles) were dissolved in 50% aqueous acetonitrile (1 ml) and cooled in an icebath. $Ca(OCl)_2$ (65% assay, 2.88 mg, 13.1 μmoles) dissolved in water (100 μl) and cooled in an icebath was added with stirring. After stirring for 4 h 2.8 ml of aqueous $NH_4OAc$ (20 mM, pH 5.4) were added. The mixture was purified by HPLC (1×25 cm C4 column; Buffer A=20 mM $NH_4OAc$ pH 5.4 in water, Buffer B=$CH_3CN$; 0 min, 100% A; 0.1–20 min, 10% to 30% B; flow rate=4 ml/min; 310 nm). Lyophilization yielded 1-NCM-2-oxo-3-HO-LSD (1.62 mg, 30%) as an off-white foam. $^1H$ NMR (200 MHz, $CD_3CN$) ppm: 1.09 (3H, t, J=3.8 Hz, $NCH_2CH_3$); 1.22 (3H, t, J=3.8 Hz, $NCH_2CH_3$); 2.46 (3H, s, $NCH_3$); 3.18 (1H, m); 3.33 (2H, m, J=3.8 Hz, $NCH_2CH_3$); 3.43 (2H, q, J=3.8 Hz, $NCH_2CH_3$); 3.85 (2H, m); 3.97 (1H, d, J=9.4 Hz, $NCH_2COOH$); 4.09 (1H, d, J=9.4 Hz, $NCH_2COOH$); 6.35 (1H, s, C=CH); 6.54 (1H, d, J=4.6 Hz, ArH); 7.19 (2H, m, ArH). MS (EI, bis-TMS derivative): 557 (M+).

Example 1C

Coupling of 1-NCM-2-oxo-3-HO-LSD with Maleimidopentylamine (MPA)

MPA-HCl (2.27 mg, 10.4 μmoles), O-benzotriazol-1-yl-N,N,N',N'-tetramethyluronium hexafluorophosphate (HBTU) (3.94 mg, 10.4 μmoles), 1-hydroxybenzotriol hydrate (HOBt) (1.41 mg, 10.4 μmoles) and diisopropyl-ethylamine (DIEA) (7.39 mg, 57.2 μmoles) were added with stirring to 1-NCM-2-oxo-3-HO-LSD (2.15 mg, 5.20 μmoles) in 400 μl DMF. After 10 min 1.4 ml of 0.1% aq. TFA were added to the mixture. The resulting solution was purified by HPLC (1×25 cm C4 column; 0 min, 100% A; 0.1–20 min, 10 to 50% B; flow rate=4 ml/min; 310 nm). Lyophilization gave 1-NCMMPA-2-oxo-3-HO-LSD (1.23 mg, 41%) as an off-white foam. $^1H$ NMR (200 MHz, $CD_3CN$) ppm: 1.08 (3H, t, J=4.0 Hz, $NCH_2CH_3$); 1.20 (3H, t, J=3.9 Hz, $NCH_2CH_3$); 1.22 (2H, m, J=3.8 Hz); 1.44 (2H, m, J=3.8 Hz); 1.52(2H, m, J=3.8 Hz); 2.39 (3H, s, $NCH_3$); 3.11 (3H, m, J=3.5 Hz); 3.38 (6H, m, J=4.0 Hz); 3.70 (1H, m); 3.78 (1H, m); 4.12 (1H, d, J=9.0 Hz, $NCH_2COOH$); 4.21 (1H, d, J=9.4 Hz, $NCH_2COOH$); 6.40(1H, s, C=CH); 6.62 (1H, dd, J=0.5, 3.8 Hz, ArH); 6.71 (2H, s, maleimide); 7.26 (2H, m, ArH). MS (electrospray): 578.3 (M+).

Example 1D

Preparation of KLH(2-IT)-1-NCMMPA-2-oxo-3-hydroxy-LSD Immunogen

2-Iminothiolane (2-IT) (4.5 mg, 10.9 μmoles) was added to KLH (20 mg) in 2.0 ml of phosphate buffer (83 mM, pH=7.2, 0.9 M NaCl) with stirring. After 150 min the mixture was desalted with a PD-10 pre-packed SEPHADEX G-25 ion exchange column (Pharmacia, Inc.) pre-equilibrated with phosphate buffer (100 mM, pH=7) to remove excess 2-IT. Half (1.5 ml) of the eluate was added to 1-NCMMPA-2-oxo-3-HO-LSD (1.77 mg, 3 µmoles) in 1.5 ml DMSO. After stirring for 5 hours the mixture was dialyzed against 800 ml phosphate buffer (10 mM, pH=7, 150 mM NaCl) and 200 ml DMF. After 12 hours the buffer was replaced. After an additional 12 hours this buffer was replaced with 2 L of phosphate buffer (10 mM, pH=7, 150 mM NaCl) which was again replaced after another 12 hours. Twelve hours after the last buffer replacement the immunogen was transferred to a vial and stored at −80° C. until used.

Example 2

Conjugation of 1-NCMMPA-2-oxo-3-hydroxy-LSD to ED28

A solution of desalted ED28 (1 mg, 102 nmoles) in 530 µl phosphate buffer (100 mM, pH 7) was added with stirring to a solution of 1-NCMMPA-2-oxo-3-hydroxy-LSD (354 µg, 613 nmoles) in 300 µl DMSO. After standing at room temperature for 1 hour, 1 ml of 20 mM NH$_4$OAc (pH 5.4 in water) was added and the mixture was purified by HPLC (C4 1×25 cm, 0 min, 100% A; 0.1–20 min, 20–40% B; flow rate=4 ml/min; 280 nm). The total volume of eluate was 4.73 ml. The yield was 521 µg (47%) as determined by UV absorbance at 280 nm ($\epsilon_{280}$=37,000). This solution was stored at −80° C. until further use.

Example 3

Preparation of Monoclonal Antibodies

Preparation of the immunogen and immunization of the host animal can be accomplished using techniques which are well known to those skilled in the art. The immunogens prepared in Example 1D are administered to mice in a series of injections. Hybridoma cell lines are then developed from fusions using immunized spleens. Supernatant antibody is evaluated as described below, and ascites is produced from useful clones. Ascites is then purified, yielding monoclonal antibody. All of the biological and purification methods can be performed in a manner well known to those skilled in the art.

For example, supernatant antibodies can be selected from 96-well culture plates using a CEDIA homogeneous assay. As previously described, the CEDIA assay utilizes two genetically engineered, enzymatically inactive fragments of β-galactosidase. The smaller polypeptide, the enzyme donor, can recombine spontaneously, with the larger fragment, the enzyme acceptor, to form active β-galactosidase, in a process called complementation. When a specific antibody to the ligand or analyte attaches to the enzyme donor conjugate, complementation is inhibited. The addition of free ligand to this system will modulate the inhibition of complementation. This assay principle is used to screen fusion products in a 96-well format.

A primary screening of the fusion products can be first performed to evaluate the ability of the antibodies to bind to the enzyme donor conjugate prepared in Example 2 and to inhibit complementation. The number of inhibition-positive clones are then narrowed further by performing a secondary screening assay to determine whether the free drug would modulate or compete with the enzyme donor conjugate for the antibody. The modulation assay also identified specific clones when screened against cross-reacting analytes. The clones which modulated with the specific analytes of choice are then grown for further study. The culture supernatants containing the monoclonal antibodies are collected and further evaluated for the desired specificity and cross-reactivity.

All publications, patents, and patent applications mentioned in this specification are hereby incorporated by reference herein to the same extent as if each individual publication, patent, or patent application were specifically and individually indicated to be incorporated by reference.

The invention now being fully described, it will be understood that the specification and examples are illustrative but not limiting of the present invention, and that modifications and changes will suggest themselves to those skilled in the art but will not depart from the spirit and scope of the appended claims.

We claim:
1. A compound of the formula

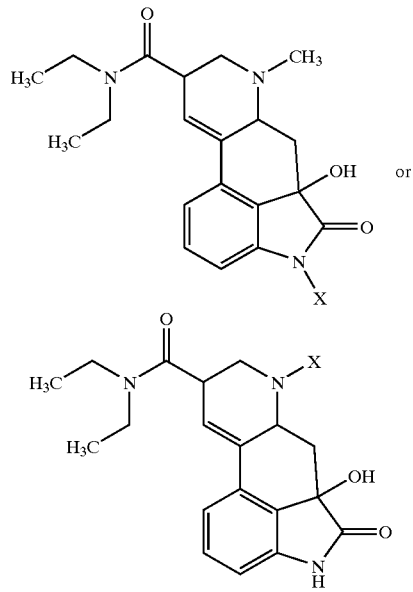

wherein X is —L$^1$—Z, where L$^1$ is a linker containing at least one carbon atom;

wherein Z is selected from the group consisting of
—NH$_2$,
—COOH,
—SH,

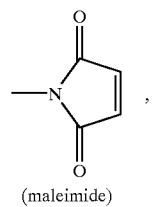

(maleimide)

—NH—C(=O)—L²—M,

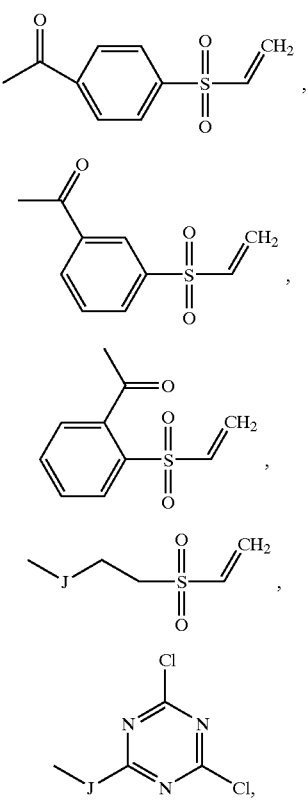

and a moiety which reacts with a protein to form a covalent bond;

where L² is a linker containing at least one carbon atom;

where M is halide or maleimide; and wherein J is —O—, —S—, —NH— or —CH₂—.

2. The compound of claim 1, wherein Z is:

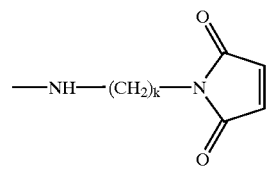

and k is an integer from 1 to 10.

3. The compound of claim 1, further derivatized via X by attachment to a member selected from the group consisting of fluorescent, chemiluminescent, phosphorescent, and chromophoric compounds, a fluorescence quenching group, a radioisotopically labeled group, an electrochemically active group, an electrochemiluminescent group, a group that undergoes a change in fluorescence, phosphorescence, chemiluminescence or electrochemical property upon binding, peptides, proteins, protein fragments, immunogenic carriers, enzymes, enzyme donors, enzyme inhibitors, enzyme substrates, enzyme cofactors, enzyme prosthetic groups, solid particles, gold particles, antibodies, and nucleic acids.

4. The compound of claim 1, further derivatized by attachment to an immunogenic polypeptide.

5. The compound of claim 1, further derivatized by attachment to keyhole limpet hemocyanin.

6. The compound of claim 1, further derivatized by attachment to an enzyme donor polypeptide.

7. The compound of claim 6, where the enzyme donor polypeptide is an enzyme donor polypeptide of β-galactosidase.

8. The compound of claim 2, further derivatized via Z by attachment to a label selected from the group consisting of an enzyme, a luminescent substance and a radioactive substance.

9. The compound of claim 1 prepared by
   (a) first derivitizing LSD to form a N-1 or N-6 carboxymethyl-LSD,
   (b) oxidizing the product of (a) to form a 2-oxo-3-hydroxy-LSD, and
   (c) further derivatizing the product of (b) with a compound comprising at least Z.

* * * * *

UNITED STATES PATENT AND TRADEMARK OFFICE
CERTIFICATE OF CORRECTION

PATENT NO.    : 6,548,645 B1
DATED         : April 15, 2003
INVENTOR(S)   : Sanchez et al.

It is certified that error appears in the above-identified patent and that said Letters Patent is hereby corrected as shown below:

Column 4,
Line 14, "2PATENT -oxo-3-hydroxy-LSD" and should read -- 2-oxo-3-hydroxy-LSD --.

Column 15,
Line 13, "a manual" and should read -- a mammal --.

Column 17,
Lines 5-6, "compounds flourescent" and should read -- compounds, flourescent --.

Column 18,
Lines 66-67, "better. preferably" and should read -- better, preferably --.

Column 20 ,
Line 28, "have. the" and should read -- have the --.

Column 22
Line 4, "$10^{10}$" and should read -- $10^{11}$ --.

Column 23
Lines 44-45, "4,264,968" and should read -- 4,261,968 --.

Column 24,
Line 47, "Gin" and should read -- Gln --.

Column 25,
Line 6, "approach; in" and should read -- approach, in --.

Column 26,
Lines 10-11, "sample or" and should read -- sample, or --.

UNITED STATES PATENT AND TRADEMARK OFFICE
CERTIFICATE OF CORRECTION

PATENT NO.   : 6,548,645 B1
DATED        : April 15, 2003
INVENTOR(S)  : Sanchez et al.

It is certified that error appears in the above-identified patent and that said Letters Patent is hereby corrected as shown below:

Column 29,
Line 23, "pH 7)" and should read -- pH = 7) --.

Column 32,
Line 40, "derivatizing" and should read -- derivitizing --.

Signed and Sealed this

Sixth Day of January, 2004

JAMES E. ROGAN
*Director of the United States Patent and Trademark Office*